United States Patent [19]

Katada et al.

[11] 4,110,626
[45] Aug. 29, 1978

[54] METHOD FOR IMPROVING THE QUALITY OF THE FRAGRANCE OF PERFUMES USING ALIPHATIC DIBASIC ACID DIESTERS

[75] Inventors: Michihisa Katada; Katsutake Hayashi, both of Tokyo; Hakuji Katsura, Yokohama; Kenichi Tomita, Tokyo; Hideo Morohoshi; Keiichi Uehara, both of Yokohama; Hiroshi Tanaka, Ebina, all of Japan

[73] Assignee: Shiseido Co., Ltd., Tokyo, Japan

[21] Appl. No.: 763,214

[22] Filed: Jan. 27, 1977

[30] Foreign Application Priority Data

Jan. 30, 1976 [JP] Japan .................................. 51-9674

[51] Int. Cl.$^2$ .............................................. C11B 9/00
[52] U.S. Cl. ..................................... 252/522; 560/190
[58] Field of Search ........................ 252/522; 560/190

[56] References Cited
PUBLICATIONS

Chem. Abs. 57: 15351b, 1962.
Chem. Abs. 67: 76214b, 1967.
Chem. Abs. 75: 91311q, 1971.
S. Arctauder, Perfume and Flavor Chemicals, Published by the author, 1969, Monograph 1143.
Chem. Abstracts 60: 1535f, 1964.

*Primary Examiner*—Veronica O'Keefe
*Attorney, Agent, or Firm*—Sughrue, Rothwell, Mion, Zinn and Macpeak

[57] ABSTRACT

A method for improving the quality of the fragrance of a perfume or a perfume composition by adding thereto a specific perfume controlling agent which improves emission of a perfume or a perfume composition and its tenacity (fixing effect), and which is an aliphatic dibasic acid diester of the general formula:

$$R_1OCOR_2COOR_3$$

wherein $R_1$ and $R_3$, which may be the same or different, each represents a saturated branched chain alkyl group containing 4 or 5 carbon atoms, and $R_2$ represents a saturated straight chain alkylene group containing 4 carbon atoms, as an active ingredient.

7 Claims, 1 Drawing Figure

* COV IN TERMS OF 0.5 % BENZENE SOLUTION OF OCTANAL (meq/kg)

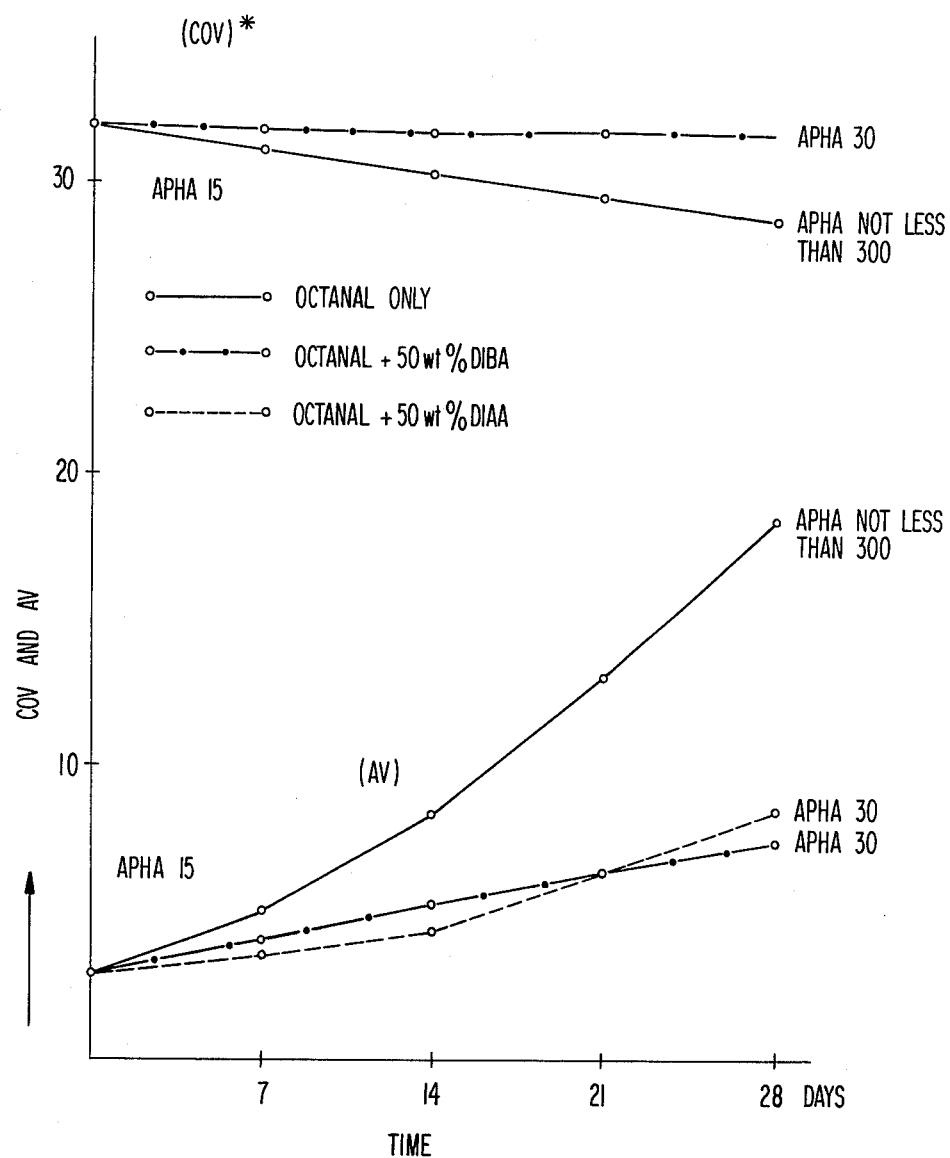

METHOD FOR IMPROVING THE QUALITY OF THE FRAGRANCE OF PERFUMES USING ALIPHATIC DIBASIC ACID DIESTERS

BACKGROUND OF THE INVENTION

1. Field of the Invention

This invention relates to a method for improving the quality of the fragrance of a perfume or a perfume composition (hereinafter, a perfume, for simplicity), and more specifically, to a method for improving the quality of the fragrance of a perfume by balancing the fragrance and maintaining the tenacity of the fragrance of the perfume by incorporating at least one perfume controlling agent in the perfume. This method improves the acceptability of the perfume by the user.

2. Description of the Prior Art

The quality of a perfume is determined by several factors. As far as its user acceptance is concerned, important factors are not only the actual odor characteristics and stability but also include the balance of the odor emission of and the tenacity of each component.

Generally, many natural or synthetic fragrant substances used as perfume materials degenerate or decay as a result of chemical changes such as polymerization, oxidation or decomposition due to the action of light, temperature, air, moisture, etc. Furthermore, they are available in a wide variety of forms ranging from low-viscosity liquids, high-viscosity resinous substances through pastes to solids. Accordingly, stabilizers must be added to chemically unstable fragrant substances, and suitable diluents must be used for high-viscosity or solid substances.

On the other hand, in order to create odors of superior quality, it is necessary to add to a perfume a substance having a fixing effect which controls the emission of odor of the fragrant substance so that a prescribed odor emission is always given off over a period of time.

Since these stabilizers, diluents and fixatives are used together with perfumes, naturally these materials must be completely safe with regard to skin irritation and toxicity, and preferably interact to reduce the skin irritation and toxicity of perfume compositions when they are incorporated therein.

Furthermore, from the viewpoint of controlling environmental pollution, these stabilizers, diluents and fixatives desirably should be biodegradable, i.e., highly assimilable by microorganisms, when discarded.

Conventionally in the production of perfumes, various controlling agents are added to perfumes in order to increase their fragrance characteristics and odor stability. In almost all cases, these controlling agents are used for a single purpose, for example, as stabilizers, diluents, or fixatives. These controlling agents are not always colorless, transparent, tasteless, and odorless compounds. Generally, odoriferous substances, such as benzyl alcohol or benzyl benzoate affect the creation of odors to a somewhat great extent. Propylene glycol, dipropylene glycol, diethyl phthalate, triethyl citrate, and isopropyl myristate, for example, are known as relatively odorless compounds, but are used only for a single purpose either as diluents or fixatives. They do not have a dual effect of stabilizing the perfumes and rendering them non-hazardous.

Propylene glycol and dipropylene glycol have low oral toxicity, and are among those perfume controlling agents which can be easily used. However, because of the comparatively high polarity of propylene glycol and dipropylene glycol, the ability to dissolve oil-soluble perfumes therein is reduced, and it is difficult to maintain a constant emission of fragrance.

The same can be said with regard to triethyl citrate. Although the oral toxicity of triethyl citrate is low, it has a high polarity like that of glycols, and is unsatisfactory in regard to the ability to dissolve oil-soluble perfumes and in regard to its fixing effect.

Diethyl phthalate is a very interesting material because its polarity is relatively suitable for use as a perfume controlling agent, and it acts both as a diluent and a fixative. However, from a safety standpoint, it has the disadvantage that its oral toxicity is high, and it is not easily biodegradable.

Isopropyl myristate has a low oral toxicity and good biodegradability, and is a superior perfume controlling agent from a safety standpoint. However, in contrast to glycols or triethyl citrate, it has so low a polarity that it has a markedly reduced ability to dissolve perfumes having a high polarity, and a uniform fragrance cannot be obtained.

Until now no ingredient which serves as a diluent, solubilizer, fixative and balancing agent with complete safety and which does not have any odor itself has been employed in perfumes to satisfy the above-mentioned requirements.

Methods are not yet known for improving the quality of the fragrance of a perfume by using perfume controlling agents which can be employed with a wide variety of perfumes.

SUMMARY OF THE INVENTION

A primary object of this invention is to provide a method for improving the quality of the fragrance of a perfume, which is free from the defects of the conventional methods.

Another object of this invention is to provide a method for improving the quality of the fragrance of a perfume, which simultaneously exhibits superior stabilizing, diluting and fixing effects.

Still another object of this invention is to provide a method for improving the quality of the fragrance of a perfume, which can be employed with a wide variety of perfumes.

A further object of this invention is to provide a method for improving the quality of the fragrance of a perfume, which is superior from the standpoint of safety in regard to skin irritation, toxicity and environmental pollution.

Aliphatic dibasic acid diesters of the general formula:

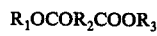

$$R_1OCOR_2COOR_3$$

wherein $R_1$ and $R_3$, which can be the same or different, each represents a saturated branched chain alkyl group containing 4 or 5 carbon atoms, and $R_2$ represents a saturated straight chain alkylene group containing 4 carbon atoms have now been extensively studied, and, as a result, it has been found that these compounds are colorless, transparent, odorless, tasteless, low viscosity liquids, that they serve as superior diluents for various odoriferous substances, and that by adding at least one of these compounds to a perfume, the fragrance characteristics and fragrance stability of the perfume can be simultaneously increased greatly. This discovery led to the accomplishment of the present invention.

According to the present invention, there is provided a method for improving the quality of the fragrance of a perfume, which comprises incorporating in the perfume at least one aliphatic dibasic acid diester of the following formula:

$$R_1OCOR_2COOR_3$$

wherein $R_1$ and $R_3$, which may be the same or different, each represents a saturated branched chain alkyl group containing 4 or 5 carbon atoms, and $R_2$ represents a saturated straight chain alkylene group containing 4 carbon atoms, as an active ingredient.

The method of this invention for improving the quality of the fragrance of a perfume is extremely safe with regard to skin irritation and toxicity.

BRIEF DESCRIPTION OF THE ACCOMPANYING DRAWING

The FIGURE shows APHA (American Public Health Association) colors of perfume compositions as determined by the APHA method, and their changes with time according to acid values (AV) and carbonyl values (COV).

DETAILED DESCRIPTION OF THE INVENTION

Perfumes to which this invention is applicable are natural perfumes such as animal or plant perfumes, isolates from natural essential oils, and synthetic perfumes. Typical examples of these perfumes are animal products such as mask, civet, castoreum, or ambergris, plant essential oils such as oakmoss, patchouli, vetiver, cedar, citronella, lemon-grass, orris, vanilla beans, rosewood, cardamon, pepper, sandalwood, star anise, cinnamon, geranium, rose, jasmin, tuberose, lime, and bergamot; artificial floral essential oils such as jasmin, rose and ylang; and synthetic perfumes, for example, hydrocarbon compounds such as limonene and α-pinene, alcohols and their esters such as linalool, geraniol, and cinnamic alcohol, aldehydes such as hydroxycitronellal and anisaldehyde, ketones such as ionone and methyl ionone, lactones, and nitrogeneous compounds such as macrocyclic musks, nitromusks, indane-series musks, and indoles. Other perfumes which can be used in this invention include those enumerated in Perfume Formulations (1) to (2) and Examples 1 to 2 described hereinafter. The above perfumes can be used either individually or as an admixture of two or more thereof.

Suitable examples of saturated branched chain alkyl groups represented by $R_1$ and $R_3$ include an isobutyl group and an isoamyl group. And a suitable example of the alkylene group represented by $R_2$ includes a butylene group.

The perfume controlling agent used in this invention includes diisobutyl adipate (DIBA for short), diisoamyl adipate (DIAA for short) and isobutyl isoamyl adipate. Of these, DIBA and DIAA are most preferred.

The perfume controlling agent concurrently possesses the effects of a stabilizer, a diluent and fixative, ensures great safety, and is odorless. It is moreover free from the defects of the conventional perfume controlling agents.

The perfume controlling agent used in this invention can be used to conveniently dilute a wide range of perfumes in the form of low viscosity liquids, resinous substances, or solids.

The amount of the perfume controlling agent employed can be varied depending on the type of perfume or fragrant preparations and the purpose of use, but is generally about 5 to about 50% by weight, preferably 10 to 30% by weight, based on the weight of the perfume. The perfume controlling agent can be used also in those systems containing a large amount of ethyl alcohol such as a perfume, an eau de Cologne, etc., without deteriorating its effect. In this case, it can be used in an amount of about 0.5 to about 20.0, preferably 1.0 to 15.0,% by weight based on the total weight of the alcohol containing system.

The perfume controlling agents can be used either individually or as an admixture of two or more thereof in mixing ratios which can be varied as described.

From the standpoint of similarity, a number of analogous compounds, such as diisopropyl adipate, dibutyl adipate, diamyl adipate, diisooctyl adipate, dioctyl adipate, diisopropyl sebacate, diisobutyl sebacate, and diisoamyl sebacate might be considered to be effective as a perfume controlling agent, but surprisingly, only those compounds of the general formula given hereinabove, such as diisobutyl adipate and diisoamyl adipate, are suitable for the purpose of the invention, and have only now been discovered for the first time as a result of attempts at achieving the objects of the invention.

The perfume controlling agent used in this invention can be prepared by reacting adipic acid with a saturated branched chain lower alcohol containing 4 or 5 carbon atoms as described in Organic Synthesis, Collective Vol. 2, pp. 264 – 265 (1943).

Some examples of preparing the compounds used as perfume controlling agents in this invention are given below. Unless otherwise indicated herein, all parts, percents, ratios and the like are by weight.

REFERENCE EXAMPLE 1

Synthesis of DIBA

A three-necked flask equipped with a stirring device and a condenser was charged with 3 moles of isobutanol, 1 mole of adipic acid and 0.01 mole of sulfuric acid, and the reaction was performed under reflux for 3 hours. Then, under reduced pressure, water formed in the reaction and the unreacted isobutanol were evaporated off. Then, 3 moles of isobutanol was freshly added, and the reaction was carried out in the same way until the reaction was completed. Again, water formed in the reaction and the excess of isobutanol were evaporated off under reduced pressure. The crude diisobutyl adipate was washed with a 5.0% by weight aqueous solution of sodium carbonate to neutralize the catalyst and remove precipitate. After removing the residue, and the product was washed several times with water. The washed product was dried, and distilled at reduced pressure to obtain 0.88 mole of a main fraction having a boiling point of 113° to 114° C/2 mmHg. The main fraction was deodorized using steam to obtain colorless, transparent, tasteless and odorless diisobutyl adipate having a purity, as determined by gas chromatography, of 99.9%.

REFERENCE EXAMPLE 2

Synthesis of DIAA

A four-necked flask equipped with a stirring device, a water-collecting tube, and a condenser was charged with 3 moles of isoamyl alcohol, 1 mole of adipic acid and 0.005 mole of p-toluenesulfonic acid. While passing nitrogen gas through the flask, an esterification reaction was performed for 4 hours. After the reaction, the crude diisoamyl adipate was washed with a dilute aqueous solution of sodium carbonate to neutralize the catalyst and remove precipitate. After removing the residue, the product was washed several times with water. The washed product was dried, and distilled at reduced pressure to obtain 0.91 mole of a main fraction having a boiling point of 151° to 153° C/4 mmHg. The main fraction was then deodorized with steam to obtain colorless, transparent, tasteless, and odorless diisoamyl adipate having a purity, as determined by gas chromatography, of 99.9%.

The skin irritation and toxicity of the perfume controlling agents used in this invention are described below.

The primary irritation of the skin of an albino rabbit was determined by adhering 0.3 ml of a test agent on a lint cloth patch, applying the cloth to an intact area and an abraded area of the skin of the back of the albino rabbit, and evaluating the skin reactions at these two areas after a lapse of 24 hours. Then, an overall evaluation was made.

The cumulative irritation on the skin of a guinea pig was evaluated by coating 0.3 ml of a test agent on intact skin of the guinea pig and judging the skin reaction after a lapse of 24 hours, then coating the test agent in an amount of 0.3 ml on the same site twice, each at 24 hour intervals, and judging the reaction of the skin after a lapse of 72 hours (after coating three times).

The controlling agents used in this invention (e.g., DIBA and DIAA) did not exhibit irritating effects both in the primary irritation test on the skin of a rabbit and the cumulative irritation test on the skin of a guinea pig described above.

The acute oral toxicity ($LD_{50}$) of the controlling compounds of this invention and conventional perfume controlling agents was also tested, and the results obtained are shown in Table 1 below.

Table 1

| Perfume Controlling Agent | $LD_{50}$ (ml/kg) |
| --- | --- |
| Diethyl Phthalate | 4.8 |
| Triethyl Citrate | >25 |
| Propylene Glycol | 23.9 |
| Dipropylene Glycol | 17.6 |
| Isopropyl Myristate | >25 |
| DIBA | 12.3 |
| DIAA | >25 |

The data shown in Table 1 demonstrate that DIBA and DIAA used in this invention have an acute toxicity equal to, or lower than, other conventional perfume controlling agents.

Typical perfume formulations whose fragrance has been improved of the quality by the method of this invention are given below.

| Perfume Formulation (1) Floral-Bouquet Type | % by Weight |
| --- | --- |
| Linalool | 4.0 |
| Bergamot Oil | 4.0 |
| Linalyl Acetate | 1.5 |
| Absolute Jasmin Oil | 5.0 |
| Essential Rose Oil | 0.5 |
| Ylang Ylang Oil | 4.0 |
| Eugenol | 1.5 |
| Isoeugenol | 2.0 |
| Vetiveryl Acetate | 2.5 |
| Hydroxycitronellal | 9.0 |
| α-Isomethyl Ionone | 3.5 |
| Benzyl Salicylate | 10.0 |
| Phenyl Ethyl Alcohol | 9.0 |
| Musk Ketone | 6.5 |
| Lemon Oil | 1.0 |
| Decanal, 1% ethyl alcohol solution | 1.0 |
| Dodecanal, 1% ethyl alcohol solution | 1.0 |
| Geraniol | 4.0 |
| Vertofix Coeur | 3.0 |
| Heliotropin | 2.0 |
| Santalex | 1.0 |
| DIBA | 24.0 |
| Total | 100.0 |

(Added Musk Ketome and Heliotropin to Benzyl Salicylate, Phenyl Ethyl Alcohol and DIBA which were comparatively stable at high temperatures and solubilized subsequently cooled them down to room temperature, and added the rest of the formulated materials.)

| Perfume Formulation (2) Cologne Type | % by Weight |
| --- | --- |
| Bergamot Oil | 10.0 |
| Galaxolide 50 | 6.0 |
| Ylang Ylang (syn.) | 3.0 |
| Musk Ketone | 3.0 |
| Benzyl Salicylate | 6.5 |
| Coumarin | 1.0 |
| γ-Methyl Ionone | 1.5 |
| α-Hexyl Cinnamic Aldehyde | 5.5 |
| Indole, 10% ethyl alcohol soluton | 0.5 |
| Galbanum Oil | 2.0 |
| Lavandin 28/30 Oil | 3.0 |
| Linalyl Acetate | 6.0 |
| Petitgrain Bigarade Oil | 4.0 |
| Coriander Oil | 2.0 |
| Lemon Oil | 5.0 |
| Sandalwood Oil | 2.0 |
| Absolute Oakmoss | 1.0 |
| Octanal, 10% ethyl alcohol solution | 2.0 |
| Decanal, 10% ethyl alcohol solution | 1.5 |
| Leaf Alcohol | 1.5 |
| Geranyl Acetate | 1.0 |
| Essential Rose Oil | 5.0 |
| DIBA | 20.0 |
| DIAA | 7.0 |
| Total | 100.0 |

(Added Musk Ketome and Heliotropin to Benzyl Salicylate, DIAA and DIBA which were comparatively stable at high temperatures and Solubilized subsequently cooled them down to room temperature, and added the rest of the formulated materials.)

The following Examples are given to specifically illustrate the advantages of the present invention.

EXAMPLE 1

Diluting Effect

The perfumes to be diluted were selected according to chemical structure and physical forms. Where the solute was a liquid, each of the controlling agents and the solute was used in a volume ratio of 1:1. When the solute was a solid, 10 ml of the controlling agent was used per gram of the solute. The diluting effects of the controlling agents were evaluated, and the results are shown in Table 2.

The changes in fragrance were evaluated by a panel of five expert perfumers.

Table 2

| Perfume | DIBA S | DIBA FC | DIAA S | DIAA FC | Dipropylene Glycol S | Dipropylene Glycol FC | Benzyl Alcohol S | Benzyl Alcohol FC | Diethyl Phthalate S | Diethyl Phthalate FC | Benzyl Benzoate S | Benzyl Benzoate FC |
|---|---|---|---|---|---|---|---|---|---|---|---|---|
| Limonene | O | O | O | O | O | O | O | Δ | O | O | O | O |
| Linalool | O | O | O | O | O | O | O | Δ | O | O | O | O |
| Linalyl Acetate | O | O | O | O | O | O | O | Δ | 0 | O | O | O |
| Laurinal | O | O | O | O | × | O | O | × | 0 | O | O | Δ |
| Ionone | O | O | O | O | O | O | O | Δ | O | O | O | O |
| Ylang Ylang | O | O | O | O | O | O | O | O | O | O | O | O |
| Coumarin | O | O | O | O | × | O | O | Δ | O | O | O | O |
| Heliotropin | O | O | O | O | O | O | O | × | O | O | O | O |
| Musk Ketone | O | O | O | O | × | O | O | × | O | O | O | O |
| Resinoid Olibanum | O | O | O | O | O | O | O | Δ | O | O | O | O |

Note
FC: Fragrance change
O: Almost no change occurred
Δ: Somewhat changed
×: Changed
S: Solubility
O: Soluble
Δ: Slightly soluble
×: Almost insoluble It can be seen from the results shown in Table 2 above that the controlling agents in accordance with this invention have a good ability to dissolve various perfumes, and because of their colorless, tasteless and odorless nature, they do not cause changes in the fragrances of the perfumes to occur after dilution.

EXAMPLE 2

Fixing Effect

A model perfume formulation was prepared using eight typical perfumes having different chemical structures, and the fixing effect of a perfume controlling agent was evaluated.

(A) Gas chromatographic analysis of the head space

The fixing effect of the perfume controlling agent was determined using a head space gas chromatographic (I) method (to be abbreviated hereinafter as HS-GC (I) method). Specifically, 0.5 g of a perfume containing the perfume controlling agent was placed in an Erlenmeyer flask, and after sealing, the flask was allowed to stand at 35° C for 60 minutes. The volatilized portion was collected and gas chromatographically analyzed under the conditions shown in Table A below.

TABLE A

Column: 3% polyethylene glycol having a molecular weight of about 20,000 on diatomaceous earth (2m)
Column Temperature: −40° C (5 minutes, isothermal) flushed to 80° C and then to 200° C (4° C/min.)
Injector Temperature: 250° C
Detector Temperature: 250° C
Detector: Flame Ionization Detector
Carrier Gas: He (40 ml/min.)

The results obtained are shown in Table 3 below.

Table 3

| Perfume | Content (% by weight) | Head Space Analysis of the Perfume Alone (%) | Head Space Analysis of the Perfume after Adding 50% of DIBA (%) |
|---|---|---|---|
| Limonene | 5.5 | 53.4 | 57.5 |
| Nonanal | 1.1 | 1.7 | 2.1 |
| Linalool | 11.0 | 15.0 | 12.8 |
| Linalyl Acetate | 11.0 | 4.1 | 0.1 |
| Benzyl Acetate | 11.0 | 12.5 | 12.6 |
| Geraniol | 16.5 | 0.9 | 0.5 |
| Rose P | 16.5 | 5.1 | 4.4 |
| Lily Aldehyde | 27.5 | 0.4 | 0.2 |

Then, the fixing effect was evaluated by a second head space gas chromatographic (II) method (HS-GC (II)). Specifically, a perfume containing 0.7 g of a perfume controlling agent was coated on a sheet of paper having a predetermined thickness, area (11.5 × 7.5 cm), and weight (about 2.9 g). The coated paper was allowed to stand for 15 minutes in an open space in a room (6 × 4 × 2.5 m) maintained at a humidity of 50% at a ventilation rate of 1,500 m³/hr. The paper was then transferred into a 1,000 ml Erlenmeyer flask, and the flask was tightly sealed. After a lapse of 15 minutes, the volatilized portion was collected and analyzed by gas chromatography under the conditions shown in Table A above. Furthermore, the residue on the paper was extracted with acetone, and analyzed by gas chromatography using conditions shown in Table B below.

TABLE B

Column: 5% FFAP (free fatty acid polyester; a trade name for a product of Nippon Chromato Co., Ltd.) on diatomaceous earth (2m)
Column Temperature: 80° C (5 minutes, isothermal) to 220° C (4° C/min.)
Injector Temperature: 260° C
Detector Temperature: 260° C
Detector: Flame Ionization Detector
Carrier Gas: He (40 ml/min.)

The results obtained are shown in Tables 4 and 5 below.

The composition of the model perfume used was as follows:

|  | % by Weight | Area (%) by Gas Chromatography* |
|---|---|---|
| Pinene | 20 | 22.0 |
| Limonene | 30 | 33.0 |
| Linalool | 20 | 20.5 |
| Linalyl Acetate | 21 | 18.5 |
| Citral | 4 | 4.5 |
| Musk Ketone | 5 | 1.5 |

*The model perfume was gas chromatographed, and the area (%) was calculated from the resulting gas chromatogram.

Table 4

Analysis of Volatilized Portion after Standing 15 Minutes (HS-GC (II) Method)

| Perfume | Perfume Controlling Agent | | | | |
|---|---|---|---|---|---|
| | Not Present (%) | DIBA Blended (%) | DEP Blended (%) | BB Blended (%) | DPG Blended (%) |
| Pinene | 0.2 | 2.4 | 0.9 | 1.3 | 0.2 |
| Limonene | 2.6 | 45.9 | 31.3 | 31.3 | 2.7 |
| Linalool | 45.2 | 29.7 | 40.5 | 37.7 | 42.8 |
| Linalyl Acetate | 39.0 | 16.4 | 18.4 | 20.6 | 40.0 |
| Citral | 3.5 | 1.3 | 1.2 | 1.6 | 3.7 |
| Musk ketone | 0.0 | 0.0 | 0.0 | 0.0 | 0.0 |

DEP, BB and DPG are abbreviations for diethyl phthalate, benzyl benzoate and dipropylene glycol, respectively.

The composition of the perfume which did not contain a perfume controlling agent was as follows:

Model Perfume: 5% by weight
95% Ethanol: 95% by weight

The composition of the perfume containing a perfume controlling agent was as follows:

Model Perfume: 5% by weight
Perfume Controlling Agent: 15% by weight
95% Ethanol: 80% by weight Table 5

Analysis of Residue on Paper after Standing 15 Minutes

| | | Perfume Controlling Agent | | | | |
|---|---|---|---|---|---|---|
| Component | Not Present | DIBA Blended (%) | DEP Blended (%) | BB Blended (%) | DPG Blended (%) | DOA Blended (%) |
| Pinene | 0.0* | 0.0 | 0.0 | 0.0 | 0.0 | 0.0 |
| Limonene | 0.3 | 0.6 | 0.5 | 0.38 | 0 | 0.7 |
| Linalool | 6.4 | 9.5 | 11.5 | 8.1 | 4.9 | 8.1 |
| Linalyl Acetate | 5.1 | 8.5 | 9.8 | 8.0 | 4.1 | 7.6 |
| Citral | 1.5 | 2.0 | 1.9 | 1.8 | 1.1 | 1.7 |
| Musk Ketone | 1.0 | 1.0 | 1.0 | 1.0 | 1.0 | 1.0 |

*Area Ratio (%)

The values shown in Table 5 above were obtained by calculating the areas of the perfumes while the area of musk ketone measured by gas chromatography was taken as 1. (This calculating procedure was adopted because musk ketone has a high boiling point, and scarcely volatilizes at 30° C.)

It can be seen from the results shown in Tables 3, 4 and 5 above that DIBA has a balanced volatility and fixing ability like DEP and BB.

(B) Sensory testing on the fixing ability of the above model perfume in powdery cosmetics (pressed powder).

Sensory testing on the fixing ability of the above model perfume in powdery cosmetic was conducted using the following pressed powder formulation.

| Pressed Powder Formulation | |
|---|---|
| | % by Weight |
| Talc | 74.0 |
| Kaolin | 10.0 |
| Titanium Dioxide | 3.0 |
| Zinc Oxide | 5.0 |
| Liquid Paraffin | 3.0 |
| Pigment | 2.0 |
| Surfactant | 1.0 |
| Lanolin | 1.0 |
| Perfume | 1.0 |
| Total | 100.0 |

Amount of Model Perfume: 1%
Amount of perfume Controlling Agent: 10% based on the model perfume (in the case of both DIBA and DIAA)
Evaluation Temperature and Period: Shelf Life Testing — 1 month later at 0° C, room temperature and 37° C, respectively
Evaluation Panel: a panel of five expert perfumers
Method of Evaluation: Comparison with a perfume which did not contain the perfume controlling agent (to be referred to as Std)

Table 6

| Evaluation of Odor | Evaluation Conditions | | |
|---|---|---|---|
| | 0° C | Room Temperature | 37° C |
| Strong > Weak Good Change | Std > DIAA > DIBA > BB | DIBA > DIAA > BB > Std | DIBA > DIAA > BB > Std |
| Quality > in Quality | DIAA > DIBA > Std > BB | DIBA > DIAA > BB > Std | DIBA > DIAA > BB > Std |

Note: BB stands for benzyl benzoate.

The same results were obtained both with the face powder and with the pressed powder.

From the results shown in Table 6 above, it can be seen that the perfume controlling agents in accordance with this invention have a very effective fixing ability in the testing for perfuming powdery cosmetics such as face powder and pressed powder.

EXAMPLE 3

Stabilizing Effect

Octanal was selected as a single perfume, and the stabilizing effect of the perfume controlling agent was determined.

Amount of Perfume Controlling Agent: 50% based on the octanal (in the case of both DIBA and DIAA)

Test Temperature and Period: 37° C, one month (checked every week)

Items Evaluated: Acid value (AV), carbonyl value (COV), APHA color.

In the test, a 100 ml brown bottle boiled in water for 12 hours was used, and the head space of the bottle was purged with nitrogen gas after the octanal had been introduced into the bottle.

The standard APHA colors (American Public Health Association colors) are set down as shown in Table 7 below.

Specifically, the color of a solution obtained by diluting 1 ml of a standard original color liquid (octanal) with water exactly to a volume of 100 ml is taken as APHA No. 5, and the APHA color number is increased by a multiple of 5 (as 10, 15, 20 . . . ) for every 1 ml increase of the original liquid.

Table 7

| APHA Standard Color | Original Liquid (ml) |
|---|---|
| 5 | 1 |
| 10 | 2 |
| 15 | 3 |
| 20 | 4 |
| 25 | 5 |
| 30 | 6 |
| 35 | 7 |
| 40 | 8 |
| 50 | 10 |
| 60 | 12 |
| 70 | 14 |
| 100 | 20 |
| 150 | 30 |
| 200 | 40 |
| 250 | 50 |
| 300 | 60 |
| 350 | 70 |
| 400 | 80 |
| 450 | 90 |
| 500 | 100 |

The results obtained are plotted in the figure. Referring now to the figure, the standard color of the octanal was set at APHA 15, and 50% each of DIBA and DIAA was added to the octanal, after which changes with time were observed. It was ascertained that the color of the octanal alone changed from the original APHA 15 to more than APHA 300 after one month, whereas when 50% by weight of DIBA or DIAA was added, the APHA of the octanal was about 30 even after a lapse of 1 month, thus exhibiting superior stability.

Accordingly, it was confirmed that the controlling agents used in this invention have very good stabilizing effects on oxidation, polymerization and decomposition of the aliphatic aldehyde.

EXAMPLE 4

Microorganism Assimilation

Using *Pseudomonas aeruginosa*, a microorganism known to assimilate materials for cosmetics well, the assimilation of perfume controlling agents by microorganisms was tested.

| Culture Medium Used | | |
|---|---|---|
| Potassium Primary Phosphate | 0.05 | g |
| Potassium Secondary Phosphate | 0.25 | g |
| Magnesium Sulfate | 0.03 | g |
| Calcium Chloride | 0.03 | g |
| Ammonium Sulfate | 0.30 | g |
| Sodium Chloride | 0.03 | g |
| Deionized Water | 100 | ml |
| Perfume Controlling Agent | 1.00 | g |

Method of Cultivation 100 ml of the above liquid medium was placed in a 500 ml Sakaguchi flask, and sterilized at 120° C for 15 minutes in an autoclave in a customary manner. After cooling, the culture medium was inoculated with a prescribed amount of a suspension of the pre-cultured microorganism and cultivated at 30° C with shaking 120 times per minute.

Test Items

Changes with time in the pH, turbidity, number of living cells were determined.

The turbidity was determined as follows: 2 ml of the culture broth was collected, and the precipitate was separated with a centrifugal separator. The precipitate was washed with acetone, and suspended in 2 ml of distilled water. The turbidity (OD) of the suspension at 660 nm was measured.

The results obtained are shown in Table 8 below.

Table 8

| | Number of Days Elapsed | | | | | | | | | |
|---|---|---|---|---|---|---|---|---|---|---|
| | 0 | 2 | | | 7 | | | 14 | | |
| Perfume Controlling Agent | pH | pH | OD | Number of Living Cells | pH | OD | Number of Living Cells | pH | OD | Number of Living Cells |
| Diethyl Phthalate | 6.86 | 6.86 | 0.001 | $2.5 \times 10^6$ | 6.86 | 0.001 | $4.2 \times 10^4$ | 6.86 | 0 | $5.2 \times 10^5$ |
| Dipropylene Glycol | 6.84 | 6.84 | 0 | $3.1 \times 10^6$ | 6.82 | 0.005 | $7.2 \times 10^7$ | 6.82 | 0 | $4.7 \times 10^6$ |
| Diisopropyl Adipate | 6.90 | 6.90 | 0.005 | $4.0 \times 10^5$ | 5.32 | 0.26 | $1.9 \times 10^7$ | 4.22 | 0.46 | $<10^3$ |
| Diisobutyl Adipate | 6.94 | 4.72 | 0.152 | $2.3 \times 10^7$ | 4.42 | 0.13 | $3 \times 10^2$ | 4.40 | 0.115 | $<10^2$ |
| Diisoamyl Adipate | 6.90 | 4.74 | 0.105 | $1.6 \times 10^6$ | 4.40 | 0.05 | $<10^2$ | 4.30 | 0.055 | $<10^2$ |
| Di-2-ethylhexyl Adipate | 6.86 | 6.60 | 0.008 | $1.3 \times 10^6$ | 6.30 | 0.01 | $5.0 \times 10^7$ | 6.10 | 0.15 | $1.4 \times 10^9$ |

As is clear from the results shown in Table 8 above, diethyl phthalate, and dipropylene glycol were not assimilated, but diisopropyl adipate, diisobutyl adipate and diisoamyl adipate were assimilated very well. It was also found that di-2-ethylhexyl adipate was gradually assimilated as time passed.

It can be readily understood from the results obtained in the above Examples that the method of this invention for improving the quality of the fragrance of perfumes is superior in stabilizing, diluting and fixing effects, meets safety requirements, and can be applied to a wide variety of perfumes.

While the invention has been described in detail and with reference to specific embodiments thereof, it will be apparent to one skilled in the art that various changes and modifications can be made therein without departing from the spirit and scope thereof.

What is claimed is:

1. A method for improving the quality of the fragrance of a natural or synthetic perfume, which comprises formulating a perfume containing at least one aliphatic dibasic acid diester of the general formula:

$$R_1OCOR_2COOR_3$$

wherein $R_1$ and $R_3$, which can be the same or different, each represents a saturated branched chain alkyl group containing 4 or 5 carbon atoms, and $R_2$ represents a saturated straight chain alkylene group containing 4 carbon atoms, as an active ingredient.

2. The method as set forth in claim 1, wherein the aliphatic dibasic acid diester is diisobutyl adipate.

3. The method as set forth in claim 1, wherein the aliphatic dibasic acid diester is diisoamyl adipate.

4. The method as set forth in claim 1, wherein the aliphatic dibasic acid diester is incorporated in an amount of about 5 to about 50% by weight based on the weight of the perfume.

5. The method as set forth in claim 1, wherein the aliphatic dibasic acid diester is incorporated in an amount of 10 to 30% by weight based on the weight of the perfume.

6. The method as set forht in claim 1, wherein the perfume is an ethyl alcohol containing perfume and the aliphatic dibasic acid diester is incorporated in an amount of about 0.5 to about 20.0% by weight based on the total weight of the alcohol containing perfume.

7. The method as set forth in claim 1, wherein the perfume is an ethyl alcohol containing perfume and the aliphatic dibasic acid diester is incorporated in an amount of 1.0 to 15.0% by weight based on the total weight of the alcohol containing perfume.

* * * * *